(12) United States Patent
Tome et al.

(10) Patent No.: US 9,807,291 B1
(45) Date of Patent: Oct. 31, 2017

(54) AUGMENTED VIDEO PROCESSING

(71) Applicant: Google Inc., Mountain View, CA (US)

(72) Inventors: Basheer Tome, Mountain View, CA (US); Hayes Solos Raffle, Mountain View, CA (US)

(73) Assignee: Google Inc., Mountain View, CA (US)

( * ) Notice: Subject to any disclaimer, the term of this patent is extended or adjusted under 35 U.S.C. 154(b) by 43 days.

(21) Appl. No.: 14/534,980

(22) Filed: Nov. 6, 2014

Related U.S. Application Data

(60) Provisional application No. 61/933,060, filed on Jan. 29, 2014.

(51) Int. Cl.
| | |
|---|---|
| *H04N 5/232* | (2006.01) |
| *H04N 1/00* | (2006.01) |
| *H04N 5/77* | (2006.01) |
| *G11B 27/031* | (2006.01) |
| *G02B 27/01* | (2006.01) |
| *H04N 101/00* | (2006.01) |

(52) U.S. Cl.
CPC .......... *H04N 5/232* (2013.01); *G02B 27/017* (2013.01); *G11B 27/031* (2013.01); *H04N 1/00204* (2013.01); *H04N 5/23229* (2013.01); *H04N 5/772* (2013.01); *G02B 2027/014* (2013.01); *G02B 2027/0178* (2013.01); *H04N 2101/00* (2013.01)

(58) Field of Classification Search
CPC .......... H04N 5/00204; H04N 1/00204; H04N 5/232; H04N 5/23223; H04N 5/23232; H04N 5/772; H04N 2101/00; G02B 7/017; G02B 27/017; G02B 2027/0178; G02B 2027/014; G03B 39/00–39/06

USPC ........ 348/208.2, 211.114, 231.3–231.6, 239, 348/333.02, 333.12
See application file for complete search history.

(56) References Cited

U.S. PATENT DOCUMENTS

| | | | | |
|---|---|---|---|---|
| 5,196,938 | A * | 3/1993 | Blessinger | H04N 5/2353 348/22 |
| 6,833,865 | B1 * | 12/2004 | Fuller | G06F 17/30247 348/231.2 |
| 7,855,743 | B2 | 12/2010 | Sako et al. | |
| 9,230,250 | B1 * | 1/2016 | Parker | G06Q 20/203 |
| 2002/0057915 | A1 | 5/2002 | Mann | |
| 2003/0146981 | A1 * | 8/2003 | Bean | H04N 5/2353 348/222.1 |
| 2004/0101178 | A1 | 5/2004 | Fedorovskaya et al. | |
| 2005/0195277 | A1 | 9/2005 | Yamasaki | |

(Continued)

FOREIGN PATENT DOCUMENTS

WO   9957900   11/1999

*Primary Examiner* — Lin Ye
*Assistant Examiner* — Chriss Yoder, III
(74) *Attorney, Agent, or Firm* — McDonnell Boehnen Hulbert & Berghoff LLP

(57) ABSTRACT

Embodiments described herein may allow for dynamic image processing based on biometric data. An example device may include: an interface configured to receive video data that is generated by an image capture device; an interface configured to receive biometric data of a user of the image capture device from one or more sensors generated synchronously with the video data; and an image processing system configured to apply image processing to the video data to generate edited video data. The image processing may be based, at least in part, on the biometric data.

23 Claims, 11 Drawing Sheets

(56) References Cited

U.S. PATENT DOCUMENTS

| | | | |
|---|---|---|---|
| 2005/0203430 A1* | 9/2005 | Williams | A61B 5/1117 600/513 |
| 2006/0103731 A1* | 5/2006 | Pilu | H04N 5/2628 348/207.99 |
| 2006/0136173 A1* | 6/2006 | Case, Jr. | A63B 24/00 702/182 |
| 2008/0211916 A1 | 9/2008 | Ono | |
| 2012/0066704 A1 | 3/2012 | Agevik | |
| 2012/0130238 A1 | 5/2012 | Muraoka et al. | |
| 2012/0229661 A1 | 9/2012 | Sekiguchi et al. | |
| 2013/0127980 A1 | 5/2013 | Haddick et al. | |
| 2013/0150117 A1 | 6/2013 | Rodriguez et al. | |
| 2013/0278631 A1 | 10/2013 | Border et al. | |
| 2013/0294648 A1 | 11/2013 | Rhoads et al. | |
| 2015/0009364 A1* | 1/2015 | Anderson | G06F 17/30265 348/231.3 |
| 2015/0281549 A1 | 10/2015 | Fridental | |
| 2015/0373293 A1* | 12/2015 | Vance | H04N 5/4401 348/143 |

\* cited by examiner

AUGMENTED VIDEO PROCESSING

CROSS-REFERENCE TO RELATED APPLICATIONS

This application claims priority to U.S. Provisional Application No. 61/933,060, filed Jan. 29, 2014, which is hereby incorporated by reference in its entirety.

BACKGROUND

Unless otherwise indicated herein, the materials described in this section are not prior art to the claims in this application and are not admitted to be prior art by inclusion in this section.

Computing devices such as personal computers, laptop computers, tablet computers, cellular phones, and countless types of Internet-capable devices are increasingly prevalent in numerous aspects of modern life. Over time, the manner in which these devices are providing information to users is becoming more intelligent, more efficient, more intuitive, or less obtrusive.

The trend toward miniaturization of computing hardware, peripherals, as well as of sensors, detectors, and image and audio processors, among other technologies, has helped open up a field sometimes referred to as "wearable computing." In the area of image and visual processing and production, in particular, it has become possible to consider wearable displays that place a graphic display close enough to a wearer's (or user's) eye(s) such that the displayed image appears substantially further away, such as might be displayed on a traditional image display device. The relevant technology may be referred to as "near-eye displays."

Wearable computing devices with near-eye displays may also be referred to as "head-mountable displays" (HMDs), "head-mounted displays," "head-mounted devices," or "head-mountable devices." A head-mountable display places a graphic display or displays close to one or both eyes of a wearer. To generate the images on a display, a computer processing system may be used. Such displays may occupy a wearer's entire field of view, or occupy only a portion of a wearer's field of view. Further, head-mounted displays may vary in size, taking a smaller form such as a glasses-style display or a larger form such as a helmet, for example.

Emerging and anticipated uses of wearable displays include applications in which users interact in real time with an augmented or virtual reality. Such applications can be mission-critical or safety-critical, such as in a public safety or aviation setting. The applications can also be recreational, such as interactive gaming. Many other applications are also possible.

HMDs may allow users to easily capture visual images and sounds collected from their environment, in some cases, completely hands free. The head- or body-mounted nature of the image capture device allows the viewer of the resulting images to visually experience the scene from the same perspective as the user of the HMD. HMD-captured images and sounds may also be shared with others in a variety of ways. Image and audio data may be collected by the HMD and shared with others in real time or recorded for immediate or later playback. The HMD may also transmit captured data to a remote computing device, such as a laptop, tablet, smartphone, or the cloud for further processing.

SUMMARY

An example device may include an image processing system configured to apply image processing to captured video data based, at least in part, on biometric data collected from a user of the image capture device. The image processing may be designed to enhance the viewing experience of the captured video. For example, the device may be configured to apply slow motion or blur effects to the captured video data based on the biometric data. The device may include, or may be configured to receive biometric data from, one or more sensors. In some examples, the image capture device may be included in a wearable device. The biometric data may include, without limitation, heart rate, respiration rate and level of movement of the wearer of the device.

In one aspect, embodiments of the present disclosure provide a computing device including: (1) an interface configured to receive video data that is generated by an image capture device; (2) an interface configured to receive, from one or more sensors, biometric data of a user of the device, wherein the biometric data is generated synchronously with the video data; and (3) an image processing system configured to apply image processing to the video data to generate edited video data, wherein the image processing is based, at least in part, on the biometric data.

Further embodiments of the present disclosure provide a method including: (1) receiving, by a computing device, video data generated by an image capture device; (2) receiving, by a computing device, biometric data of a user of the image capture device from one or more sensors, wherein the biometric data is generated synchronously with the video data; and (3) applying image processing to the video data to generate edited video data, wherein the image processing is based, at least in part, on the biometric data.

Some embodiments of the present disclosure provide a non-transitory computer readable medium having stored therein instructions executable by a processor to cause a computing device to perform functions including: (1) receiving video data generated by an image capture device; (2) receiving, from one or more sensors, biometric data of a user of the image capture device, wherein the biometric data is generated synchronously with the video data; and (3) applying image processing to the video data to generate edited video data, wherein the image processing is based, at least in part, on the biometric data.

These as well as other aspects, advantages, and alternatives will become apparent to those of ordinary skill in the art by reading the following detailed description, with reference where appropriate to the accompanying drawings.

DETAILED DESCRIPTION

Figure 1A:
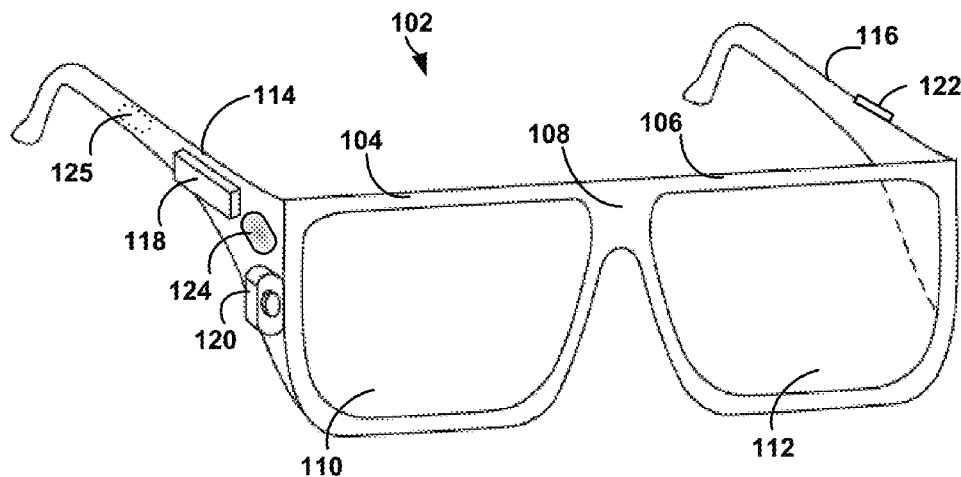
FIG. 1A illustrates a wearable computing system according to an example embodiment.

Example methods and systems are described herein. It should be understood that the words "example," "exemplary," and "illustrative" are used herein to mean "serving as an example, instance, or illustration." Any embodiment or feature described herein as being an "example," being "exemplary," or being "illustrative" is not necessarily to be construed as preferred or advantageous over other embodiments or features. The example embodiments described herein are not meant to be limiting. It will be readily understood that the aspects of the present disclosure, as generally described herein, and illustrated in the figures, can be arranged, substituted, combined, separated, and designed in a wide variety of different configurations, all of which are explicitly contemplated herein.

I. Overview

While HMDs may capture images and sounds from the viewing perspective of the wearer or operator, the raw image or audio data may not sufficiently convey the full range of emotions, stimulations, or sensations, experienced by the user, to a viewer of the recorded images. To improve the raw video captured by an HMD, video editing and special effects (slow or fast motion scenes, pauses, cuts, timed music, coloring, etc.) can be used to better evoke the feelings and sensations of the moment of capture.

Biometric data sensed from the wearer of an HMD or biometric data otherwise received by the HMD may be used to augment both front-end image capture and back-end image processing, potentially in real time. In an example system, an HMD synchronously records image, audio, and biometric data for automatic or dynamic recording or editing.

In one aspect, the received data may be used to control image capture software or hardware on an HMD. For example, data taken from biometric sensors, such as heart rate, may be used to control the HMD's camera or video software or hardware, such as by controlling the speed or resolution of image capture. In some embodiments, data received from an inertial measurement unit ("IMU") may cause the video camera to increase its rate of frame capture or resolution when it detects that it is falling. This portion of increased frame rate video may later be used to create a "slow motion" section of video during free-fall.

In another aspect, biometric data received from biometric, contextual or "movement" sensors may be used for assisted post-capture image or audio editing. Metadata from the sensors and other inputs may be synchronously recorded with the image and audio data and may be used post-capture to automatically edit or suggest edits to the image and audio data to create a more interesting or sensory-representative composition. For example, data collected from a heart-rate monitor (HRM) indicating an increase in the wearer's heart rate, may automatically (or suggest that the user) slow-down that segment of recorded video to create visual emphasis.

Biometric data may include any data related to the sensory, physiological, behavioral, health, movement, context or other measurable characteristics of a living subject or a function of the living subject, such as heart rate, pulse rate, respiration rate, body temperature, perspiration, eye movements, blinking, muscle flinches or tension, strength of hand grip, etc. Biometric data may be gathered from direct measurement of an aspect or characteristic of the body, or any data indicative of the movement or context of a body. The system may also receive certain contextual data, including GPS (or other location) data, elevation, type of movement (i.e. walking, driving, biking, swimming, etc.), weather, ambient temperature, etc. Further, motion-related data may include speed, cadence or direction of movement of the body, orientation of the body, gravitational and inertial forces acting on the body, etc.

Data may be collected from biometric, movement and contextual sensors integrated on the HMD, by sensors remote to the HMD (such as biometric sensors placed on other portions of the body or in communication with the body, or from a remote GPS-ready device such as a smartphone), by other computing devices remote from the HMD (such as a remote device such as a smartphone having location tracking and internet capabilities), or by manual input by the wearer of the HMD. Biometric sensors may include heart rate monitors, pulse oximeters, thermometers, galvanic skin response sensors, microphones, bone conducting transducers, Doppler devices, eye tracking devices, electromyographs ("EMG"), strain gauges, etc. Movement-sensors may include accelerometers, IMUs, infrared sensors, ultrasonic sensors, odometers, pedometers, etc. and may also detect position and orientation without necessarily detecting "movement." Contextual sensors may include GPS devices, thermometers, and computing devices which may receive inputs from the wearer of the HMD.

The biometric data may be used to augment real-time image capture and editing of images captured with, for example, an HMD. Certain biometric or motion data, such as a spike in heart rate or a sudden increase or decrease in an accelerometer reading, may be used as a cue to: (a) adjust image-capture hardware settings on HMD to, for example, increase frame rate or resolution (in anticipation of some post-capture editing), (b) begin a rolling video buffer in case the image-capture hardware was not recording, or (c) suggest certain edits or automatically edit the corresponding video data in post-production. Post-capture editing can occur off-device (e.g., in the cloud) using the sensor or input data uploaded along with the image and audio data.

A variety of editing techniques, including scene cuts, fade-ins, fade-outs, playback speed, music, color, light intensity, etc., may be synchronized with or used to enhance the captured image or audio data to correlate to suspense, stress, anticipation, movement, intensity, etc. Thus, the playback speed of certain video segments may be edited to correspond to the wearer's in-the-moment experiences. Data reflecting a lack of movement of the user and relatively low heart rate during a certain period may be interpreted as a relatively un-interesting video segment and may be automatically cut or sped-up or a recommendation to cut or speed-up this segment may be made by the system. On the other hand, data reflecting a high level of movement of the user, an elevated heart rate, an elevated respiration rate, increased perspiration, or a fixed eye gaze, etc. may be interpreted as a particularly exciting, interesting, or intense and, therefore, high intensity or high volume music, slow motion playback, color enhancement, etc. may be introduced or suggested. Further, the timing of the edits, such as the music's time signature and tempo or the frequency of light or color intensity flashing in the visual data, may be chosen to match and may be synchronized with the cadence of the wearer's steps, peddling, or movement or to the intensity of the wearer's physical movements.

It should be understood that the above embodiments and others described herein are provided for purposes of illustration, and are not intended to be limiting. Variations on the above embodiments and other embodiments are possible, without departing from the scope of the invention as set forth by the claims.

II. Example Wearable Computing Devices

Systems and devices in which example embodiments may be implemented will now be described in greater detail. In general, an example system may be implemented in or may take the form of a wearable computer (also referred to as a wearable computing device). In an example embodiment, a wearable computer takes the form of or includes a head-mountable device (HMD).

An example system may also be implemented in or take the form of other devices, such as a mobile phone, among other possibilities. Further, an example system may take the form of non-transitory computer readable medium, which has program instructions stored thereon that are executable by a processor to provide the functionality described herein. An example system may also take the form of a device such as a wearable computer or mobile phone, or a subsystem of such a device, which includes such a non-transitory computer readable medium having such program instructions stored thereon.

An HMD may generally be any display device that is capable of being worn on the head and places a display in front of one or both eyes of the wearer. An HMD may take various forms such as a helmet or eyeglasses. As such, references to "eyeglasses" or a "glasses-style" HMD should be understood to refer to an HMD that has a glasses-like frame so that it can be worn on the head. Further, example embodiments may be implemented by or in association with an HMD with a single display or with two displays, which may be referred to as a "monocular" HMD or a "binocular" HMD, respectively.

FIG. 1A illustrates a wearable computing system according to an example embodiment. In FIG. 1A, the wearable computing system takes the form of a head-mountable device (HMD) 102 (which may also be referred to as a head-mounted display). It should be understood, however, that example systems and devices may take the form of or be implemented within or in association with other types of devices, without departing from the scope of the invention. As illustrated in FIG. 1A, the HMD 102 includes frame elements including lens-frames 104, 106 and a center frame support 108, lens elements 110, 112, and extending side-arms 114, 116. The center frame support 108 and the extending side-arms 114, 116 are configured to secure the HMD 102 to a user's face via a user's nose and ears, respectively.

Each of the frame elements 104, 106, and 108 and the extending side-arms 114, 116 may be formed of a solid structure of plastic or metal, or may be formed of a hollow structure of similar material so as to allow wiring and component interconnects to be internally routed through the HMD 102. Other materials may be possible as well.

One or more of each of the lens elements 110, 112 may be formed of any material that can suitably display a projected image or graphic. Each of the lens elements 110, 112 may also be sufficiently transparent to allow a user to see through the lens element. Combining these two features of the lens elements may facilitate an augmented reality or heads-up display where the projected image or graphic is superimposed over a real-world view as perceived by the user through the lens elements.

The extending side-arms 114, 116 may each be projections that extend away from the lens-frames 104, 106, respectively, and may be positioned behind a user's ears to secure the HMD 102 to the user. The extending side-arms 114, 116 may further secure the HMD 102 to the user by extending around a rear portion of the user's head. Additionally or alternatively, for example, the HMD 102 may connect to or be affixed within a head-mounted helmet structure. Other configurations for an HMD are also possible.

The HMD 102 may also include an on-board computing system 118, an image capture device 120, a sensor 122, and a finger-operable touch pad 124. The on-board computing system 118 is shown to be positioned on the extending side-arm 114 of the HMD 102; however, the on-board computing system 118 may be provided on other parts of the HMD 102 or may be positioned remote from the HMD 102 (e.g., the on-board computing system 118 could be wire- or wirelessly-connected to the HMD 102). The on-board computing system 118 may include a processor and memory, for example. The on-board computing system 118 may be configured to receive and analyze data from the image capture device 120 and the finger-operable touch pad 124 (and possibly from other sensory devices, user interfaces, or both) and generate images for output by the lens elements 110 and 112.

The image capture device 120 may be, for example, a camera that is configured to capture still images or to capture video. In the illustrated configuration, image capture device 120 is positioned on the extending side-arm 114 of the HMD 102; however, the image capture device 120 may be provided on other parts of the HMD 102. The image capture device 120 may be configured to capture images at various resolutions or at different frame rates. Many image capture devices with a small form-factor, such as the cameras used in mobile phones or webcams, for example, may be incorporated into an example of the HMD 102.

Further, although FIG. 1A illustrates one image capture device 120, more image capture device may be used, and each may be configured to capture the same view, or to capture different views. For example, the image capture device 120 may be forward facing to capture at least a portion of the real-world view perceived by the user. This forward facing image captured by the image capture device 120 may then be used to generate an augmented reality where computer generated images appear to interact with or overlay the real-world view perceived by the user.

The sensor 122 is shown on the extending side-arm 116 of the HMD 102; however, the sensor 122 may be positioned on other parts of the HMD 102. For illustrative purposes, only one sensor 122 is shown. However, in an example embodiment, the HMD 102 may include multiple sensors. For example, an HMD 102 may include sensors 102 such as one or more gyroscopes, one or more accelerometers, one or more magnetometers, one or more light sensors, one or more infrared sensors, or one or more microphones. Other sensing devices may be included in addition or in the alternative to the sensors that are specifically identified herein.

The finger-operable touch pad 124 is shown on the extending side-arm 114 of the HMD 102. However, the finger-operable touch pad 124 may be positioned on other parts of the HMD 102. Also, more than one finger-operable touch pad may be present on the HMD 102. The finger-operable touch pad 124 may be used by a user to input commands. The finger-operable touch pad 124 may sense at least one of a pressure, position or a movement of one or more fingers via capacitive sensing, resistance sensing, or a surface acoustic wave process, among other possibilities. The finger-operable touch pad 124 may be capable of sensing movement of one or more fingers simultaneously, in addition to sensing movement in a direction parallel or planar to the pad surface, in a direction normal to the pad surface, or both, and may also be capable of sensing a level of pressure applied to the touch pad surface. In some embodiments, the finger-operable touch pad 124 may be formed of one or more translucent or transparent insulating layers and one or more translucent or transparent conducting layers. Edges of the finger-operable touch pad 124 may be formed to have a raised, indented, or roughened surface, so as to provide tactile feedback to a user when the user's finger reaches the edge, or other area, of the finger-operable touch pad 124. If more than one finger-operable touch pad is present, each finger-operable touch pad may be operated independently, and may provide a different function.

In a further aspect, HMD 102 may be configured to receive user input in various ways, in addition or in the alternative to user input received via finger-operable touch pad 124. For example, on-board computing system 118 may implement a speech-to-text process and utilize a syntax that maps certain spoken commands to certain actions. In addition, HMD 102 may include one or more microphones via which a wearer's speech may be captured. Configured as such, HMD 102 may be operable to detect spoken commands and carry out various computing functions that correspond to the spoken commands.

As another example, HMD 102 may interpret certain head-movements as user input. For example, when HMD 102 is worn, HMD 102 may use one or more gyroscopes or one or more accelerometers to detect head movement. The HMD 102 may then interpret certain head-movements as being user input, such as nodding, or looking up, down, left, or right. An HMD 102 could also pan or scroll through graphics in a display according to movement. Other types of actions may also be mapped to head movement.

As yet another example, HMD 102 may interpret certain gestures (e.g., by a wearer's hand or hands) as user input. For example, HMD 102 may capture hand movements by analyzing image data from image capture device 120, and initiate actions that are defined as corresponding to certain hand movements.

As a further example, HMD 102 may interpret eye movement as user input. In particular, HMD 102 may include one or more inward-facing image capture devices or one or more other inward-facing sensors (not shown) sense a user's eye movements or positioning. As such, certain eye movements may be mapped to certain actions. For example, certain actions may be defined as corresponding to movement of the eye in a certain direction, a blink, or a wink, among other possibilities.

HMD 102 also includes a speaker 125 for generating audio output. In one example, the speaker could be in the form of a bone conduction speaker, also referred to as a bone conduction transducer (BCT). Speaker 125 may be, for example, a vibration transducer or an electroacoustic transducer that produces sound in response to an electrical audio signal input. The frame of HMD 102 may be designed such that when a user wears HMD 102, the speaker 125 contacts the wearer. Alternatively, speaker 125 may be embedded within the frame of HMD 102 and positioned such that, when the HMD 102 is worn, speaker 125 vibrates a portion of the frame that contacts the wearer. In either case, HMD 102 may be configured to send an audio signal to speaker 125, so that vibration of the speaker may be directly or indirectly transferred to the bone structure of the wearer. When the vibrations travel through the bone structure to the bones in the middle ear of the wearer, the wearer can interpret the vibrations provided by BCT 125 as sounds.

Various types of bone-conduction transducers (BCTs) may be implemented, depending upon the particular implementation. Generally, any component that is arranged to vibrate the HMD 102 may be incorporated as a vibration transducer. Yet further it should be understood that an HMD 102 may include a single speaker 125 or multiple speakers. In addition, the location(s) of speaker(s) on the HMD may vary, depending upon the implementation. For example, a speaker may be located proximate to a wearer's temple (as shown), behind the wearer's ear, proximate to the wearer's nose, or at any other location where the speaker 125 can vibrate the wearer's bone structure.

Figure 1B:
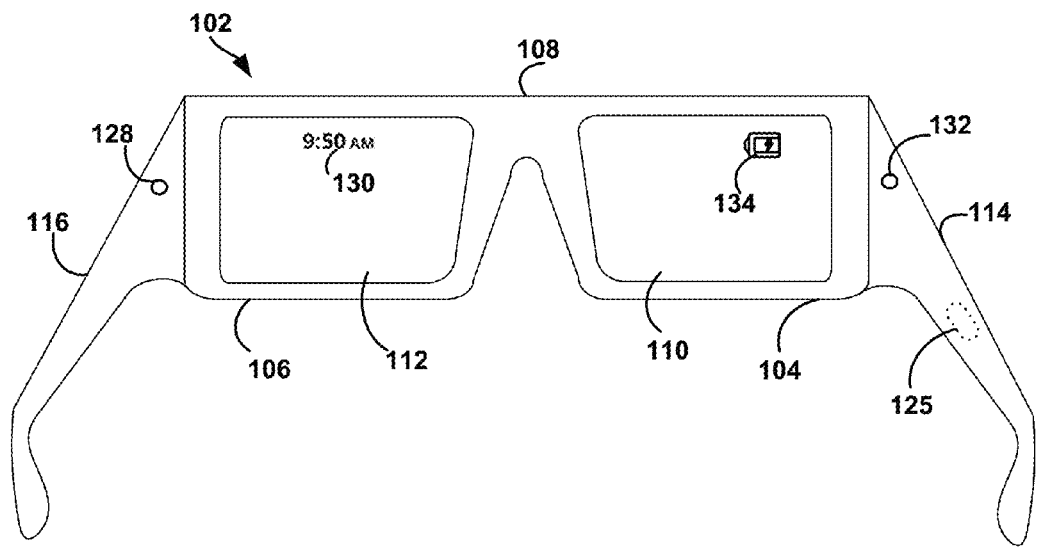
FIG. 1B illustrates an alternate view of the wearable computing device illustrated in FIG. 1A.

FIG. 1B illustrates an alternate view of the wearable computing device illustrated in FIG. 1A. As shown in FIG. 1B, the lens elements 110, 112 may act as display elements. The HMD 102 may include a first projector 128 coupled to an inside surface of the extending side-arm 116 and configured to project a display 130 onto an inside surface of the lens element 112. Additionally or alternatively, a second projector 132 may be coupled to an inside surface of the extending side-arm 114 and configured to project a display 134 onto an inside surface of the lens element 110.

The lens elements 110, 112 may act as a combiner in a light projection system and may include a coating that reflects the light projected onto them from the projectors 128, 132. In some embodiments, a reflective coating may not be used (e.g., when the projectors 128, 132 are scanning laser devices).

In alternative embodiments, other types of display elements may also be used. For example, the lens elements 110, 112 themselves may include: a transparent or semi-transparent matrix display, such as an electroluminescent display or a liquid crystal display, one or more waveguides for delivering an image to the user's eyes, or other optical elements capable of delivering an in focus near-to-eye image to the user. A corresponding display driver may be disposed within the frame elements 104, 106 for driving such a matrix display. Alternatively or additionally, a laser or LED source and scanning system could be used to draw a raster display directly onto the retina of one or more of the user's eyes. Other possibilities exist as well.

Figure 1C:
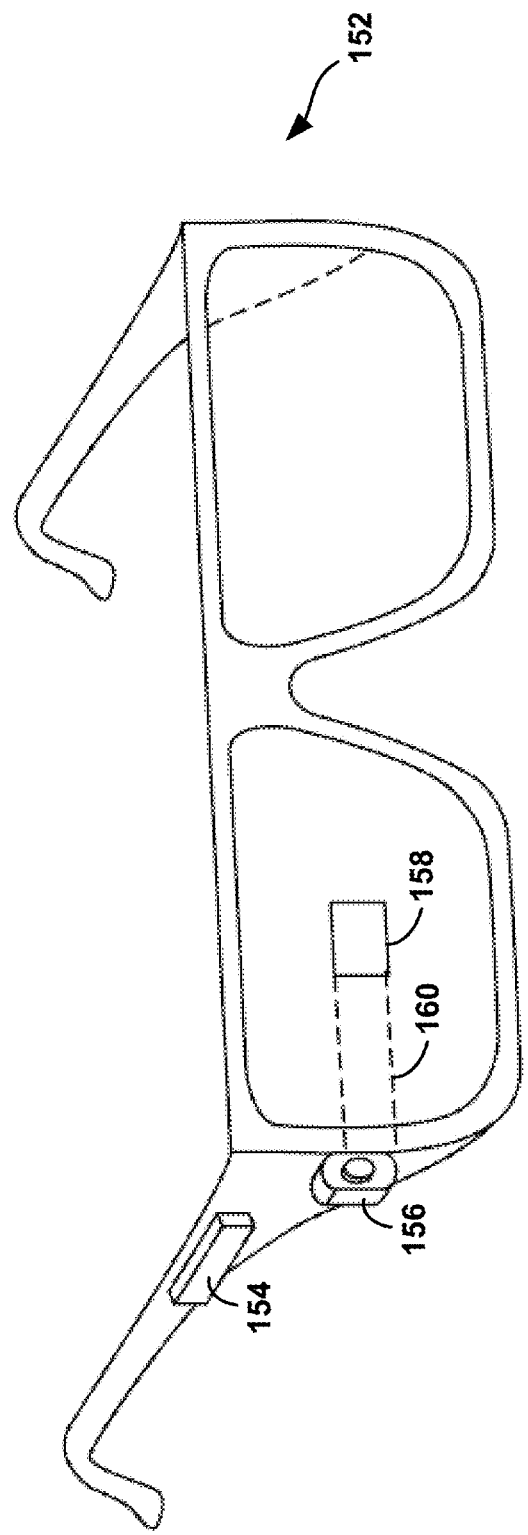
FIG. 1C illustrates another wearable computing system according to an example embodiment.

FIG. 1C illustrates another wearable computing system according to an example embodiment, which takes the form of an HMD 152. The HMD 152 may include frame elements and side-arms such as those described with respect to FIGS. 1A and 1B. The HMD 152 may additionally include an on-board computing system 154 and an image capture device 156, such as those described with respect to FIGS. 1A and 1B. The image capture device 156 is shown mounted on a frame of the HMD 152. However, the image capture device 156 may be mounted at other positions as well.

As shown in FIG. 1C, the HMD 152 may include a single display 158 which may be coupled to the device. The display 158 may be formed on one of the lens elements of the HMD 152, such as a lens element described with respect to FIGS.

1A and 1B, and may be configured to overlay computer-generated graphics in the user's view of the physical world. The display 158 is shown to be provided in a center of a lens of the HMD 152, however, the display 158 may be provided in other positions, such as for example towards either the upper or lower portions of the wearer's field of view. The display 158 is controllable via the computing system 154 that is coupled to the display 158 via an optical waveguide 160.

Figure 1D:
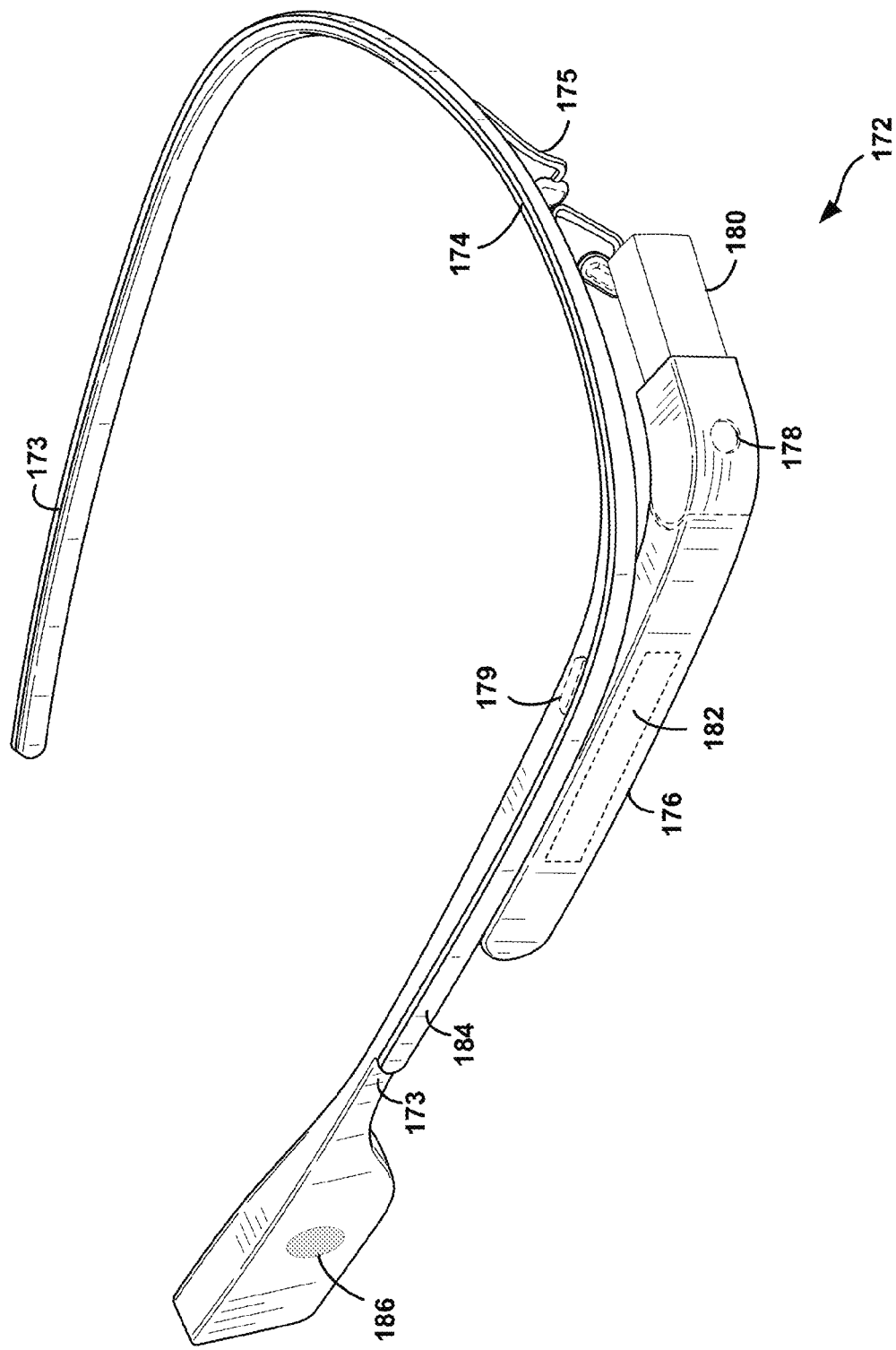
FIG. 1D illustrates another wearable computing system according to an example embodiment.

FIG. 1D illustrates another wearable computing system according to an example embodiment, which takes the form of a monocular HMD 172. The HMD 172 may include side-arms 173, a center frame support 174, and a bridge portion with nosepiece 175. In the example shown in FIG. 1D, the center frame support 174 connects the side-arms 173. The HMD 172 does not include lens-frames containing lens elements. The HMD 172 may additionally include a component housing 176, which may include an on-board computing system (not shown), an image capture device 178, and a button 179 for operating the image capture device 178 (or usable for other purposes). Component housing 176 may also include other electrical components or may be electrically connected to electrical components at other locations within or on the HMD. HMD 172 also includes a BCT 186.

The HMD 172 may include a single display 180, which may be coupled to one of the side-arms 173 via the component housing 176. In an example embodiment, the display 180 may be a see-through display, which is made of glass or another transparent or translucent material, such that the wearer can see their environment through the display 180. Further, the component housing 176 may include the light sources (not shown) for the display 180 or optical elements (not shown) to direct light from the light sources to the display 180. As such, display 180 may include optical features that direct light that is generated by such light sources towards the wearer's eye, when HMD 172 is being worn.

In a further aspect, HMD 172 may include a sliding feature 184, which may be used to adjust the length of the side-arms 173. Thus, sliding feature 184 may be used to adjust the fit of HMD 172. Further, an HMD may include other features that allow a wearer to adjust the fit of the HMD, without departing from the scope of the invention.

Figure 1E:
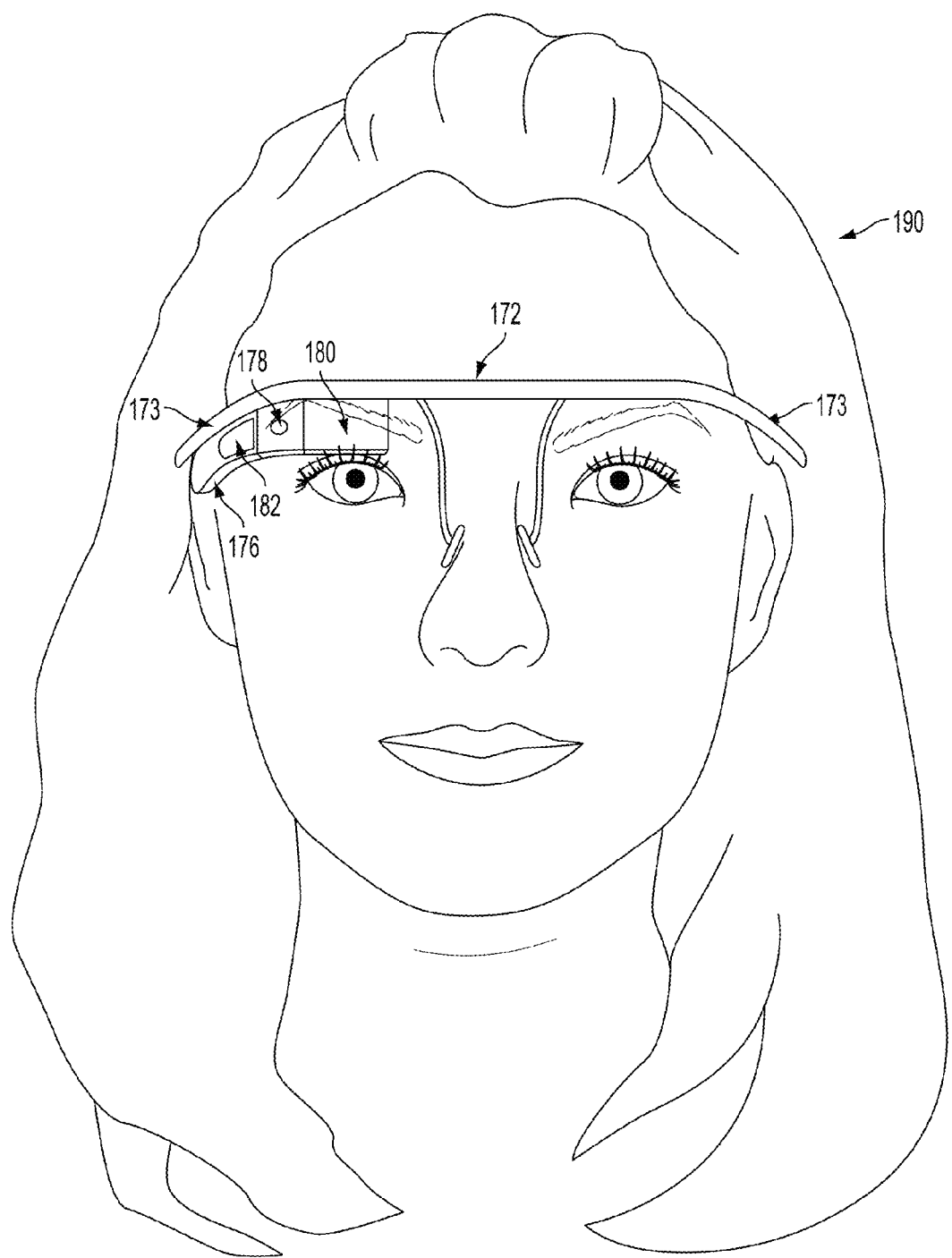
FIG. 1E is a simplified illustration of the wearable computing system shown in FIG. 1D, being worn by a wearer.
Figure 1F:
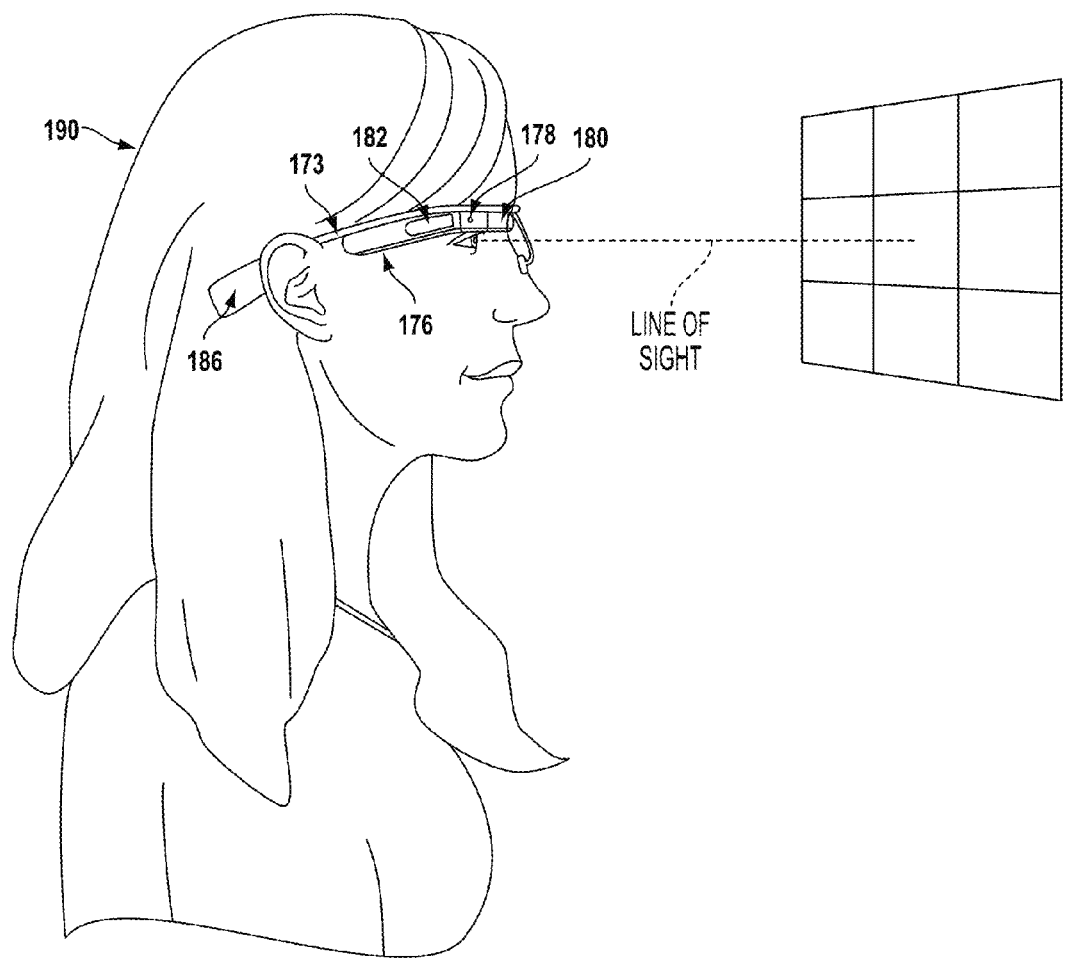
FIG. 1F is a simplified illustration of the wearable computing system shown in FIG. 1D, being worn by a wearer.
Figure 1G:
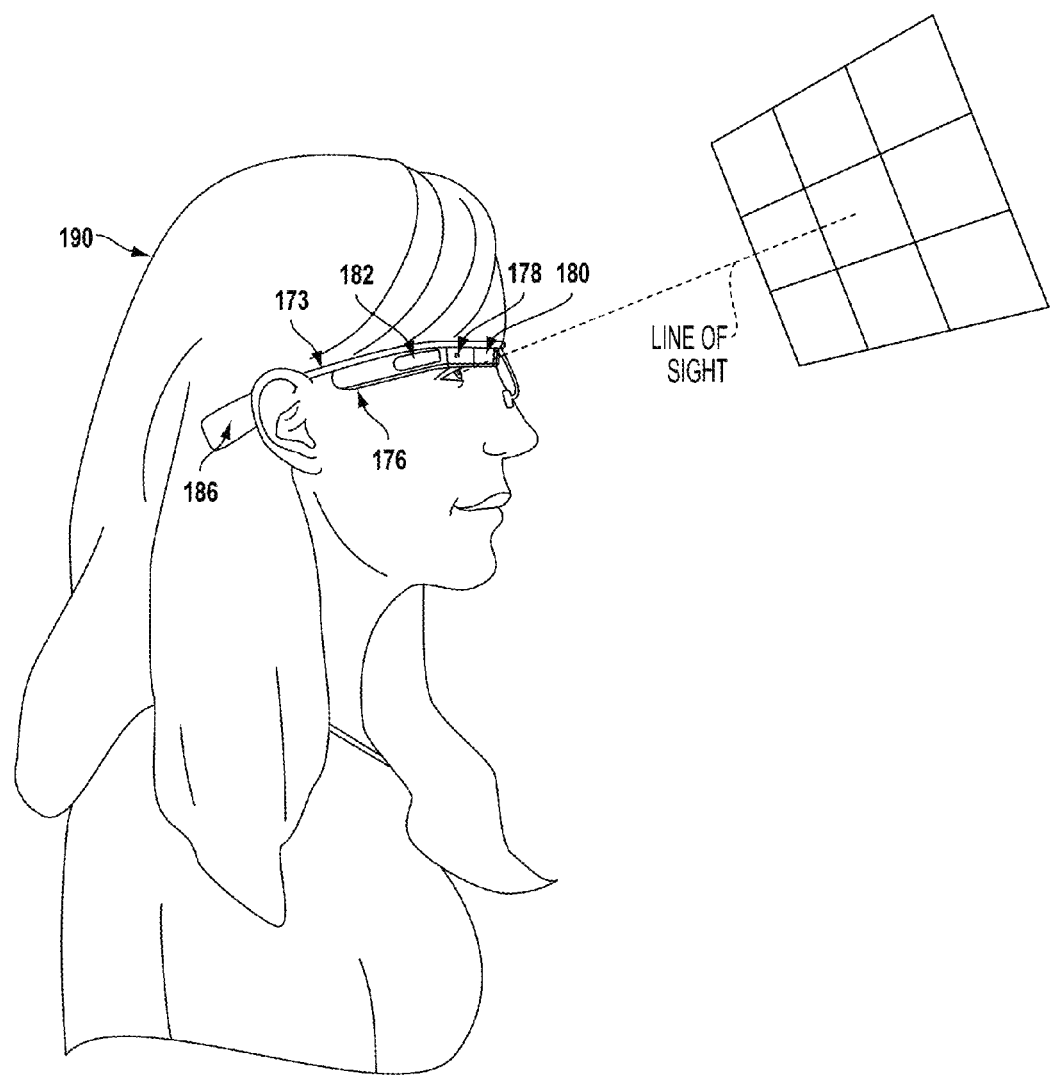
FIG. 1G is a simplified illustration of the wearable computing system shown in FIG. 1D, being worn by a wearer.

FIGS. 1E to 1G are simplified illustrations of the HMD 172 shown in FIG. 1D, being worn by a wearer 190. As shown in FIG. 1F, when HMD 172 is worn, BCT 186 is arranged such that when HMD 172 is worn, BCT 186 is located behind the wearer's ear. As such, BCT 186 is not visible from the perspective shown in FIG. 1E.

In the illustrated example, the display 180 may be arranged such that when HMD 172 is worn, display 180 is positioned in front of or proximate to a user's eye when the HMD 172 is worn by a user. For example, display 180 may be positioned below the center frame support and above the center of the wearer's eye, as shown in FIG. 1E. Further, in the illustrated configuration, display 180 may be offset from the center of the wearer's eye (e.g., so that the center of display 180 is positioned to the right and above of the center of the wearer's eye, from the wearer's perspective).

Configured as shown in FIGS. 1E to 1G, display 180 may be located in the periphery of the field of view of the wearer 190, when HMD 172 is worn. Thus, as shown by FIG. 1F, when the wearer 190 looks forward, the wearer 190 may see the display 180 with their peripheral vision. As a result, display 180 may be outside the central portion of the wearer's field of view when their eye is facing forward, as it commonly is for many day-to-day activities. Such positioning can facilitate unobstructed eye-to-eye conversations with others, as well as generally providing unobstructed viewing and perception of the world within the central portion of the wearer's field of view. Further, when the display 180 is located as shown, the wearer 190 may view the display 180 by, e.g., looking up with their eyes only (possibly without moving their head). This is illustrated as shown in FIG. 1G, where the wearer has moved their eyes to look up and align their line of sight with display 180. A wearer might also use the display by tilting their head down and aligning their eye with the display 180.

Figure 2:
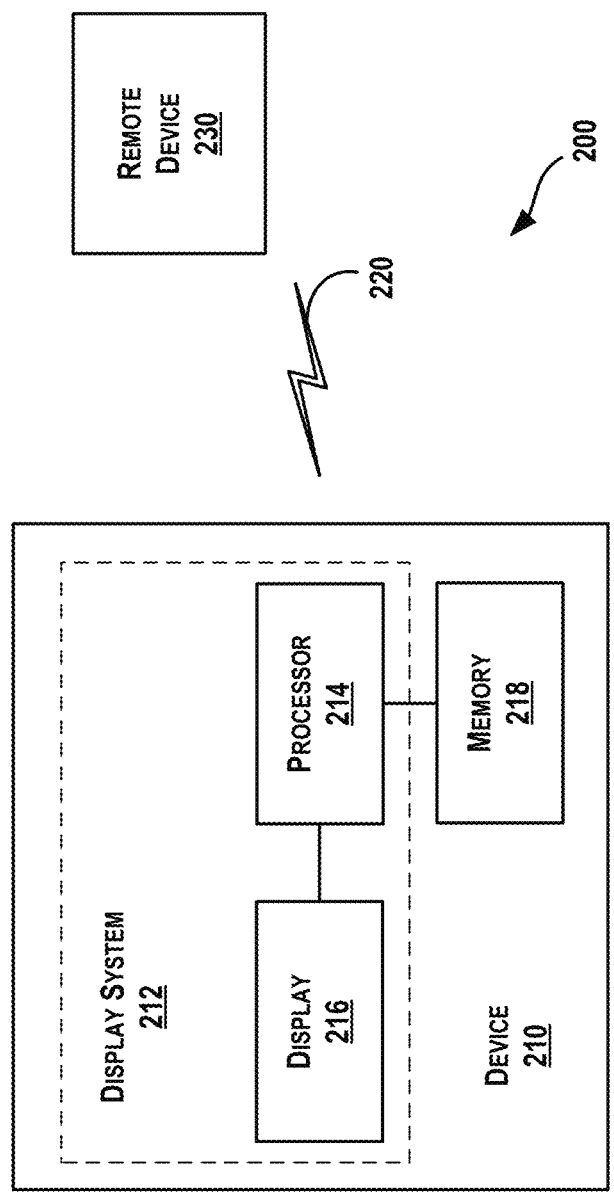
FIG. 2 is a simplified block diagram of a computing device according to an example embodiment.

FIG. 2 is a simplified block diagram a computing device 210 according to an example embodiment. In an example embodiment, device 210 communicates using a communication link 220 (e.g., a wired or wireless connection) to a remote device 230. The device 210 may be any type of device that can receive data and display information corresponding to or associated with the data. For example, the device 210 may take the form of or include a head-mountable display, such as the head-mounted devices 102, 152, or 172 that are described with reference to FIGS. 1A to 1G.

The device 210 may include a processor 214 and a display 216. The display 216 may be, for example, an optical see-through display, an optical see-around display, or a video see-through display. The processor 214 may receive data from the remote device 230, and configure the data for display on the display 216. The processor 214 may be any type of processor, such as a micro-processor or a digital signal processor, for example.

The device 210 may further include on-board data storage, such as memory 218 coupled to the processor 214. The memory 218 may store software that can be accessed and executed by the processor 214, for example.

The remote device 230 may be any type of computing device or transmitter including a laptop computer, a mobile telephone, head-mountable display, tablet computing device, etc., that is configured to transmit data to the device 210. The remote device 230 and the device 210 may contain hardware to enable the communication link 220, such as processors, transmitters, receivers, antennas, etc.

Further, remote device 230 may take the form of or be implemented in a computing system that is in communication with and configured to perform functions on behalf of client device, such as computing device 210. Such a remote device 230 may receive data from another computing device 210 (e.g., an HMD 102, 152, or 172 or a mobile phone), perform certain processing functions on behalf of the device 210, and then send the resulting data back to device 210. This functionality may be referred to as "cloud" computing.

In FIG. 2, the communication link 220 is illustrated as a wireless connection; however, wired connections may also be used. For example, the communication link 220 may be a wired serial bus such as a universal serial bus or a parallel bus. A wired connection may be a proprietary connection as well. The communication link 220 may also be a wireless connection using, e.g., Bluetooth® radio technology, communication protocols described in IEEE 802.11 (including any IEEE 802.11 revisions), Cellular technology (such as GSM, CDMA, UMTS, EV-DO, WiMAX, or LTE), or Zigbee® technology, among other possibilities. The remote device 230 may be accessible via the Internet and may include a computing cluster associated with a particular web service (e.g., social-networking, photo sharing, address book, etc.).

III. Example system

Example embodiments of a device capable of dynamically controlling at least one setting of an image device based, at least in part, on biometric data will now be described in greater detail. In general, an example device may be implemented as part of a wearable or body-mountable image-capture device (also referred to as a wearable computing device), such as a head-mountable device (HMD), as described above, a mobile phone with camera or stand-alone digital camera that may be attached or mounted to a user, such as by an arm-band, wrist band, wrist mount, or a chest-mount system, among other possibilities. Further, an example device may include a non-transitory computer readable medium, which has program instructions stored thereon that are executable by a processor to provide the functionality described herein. An example imaging device may also be implemented as part of or take the form of a wearable computer or mobile phone, or a subsystem of such a device, which includes such a non-transitory computer readable medium having such program instructions stored thereon.

Figure 3:
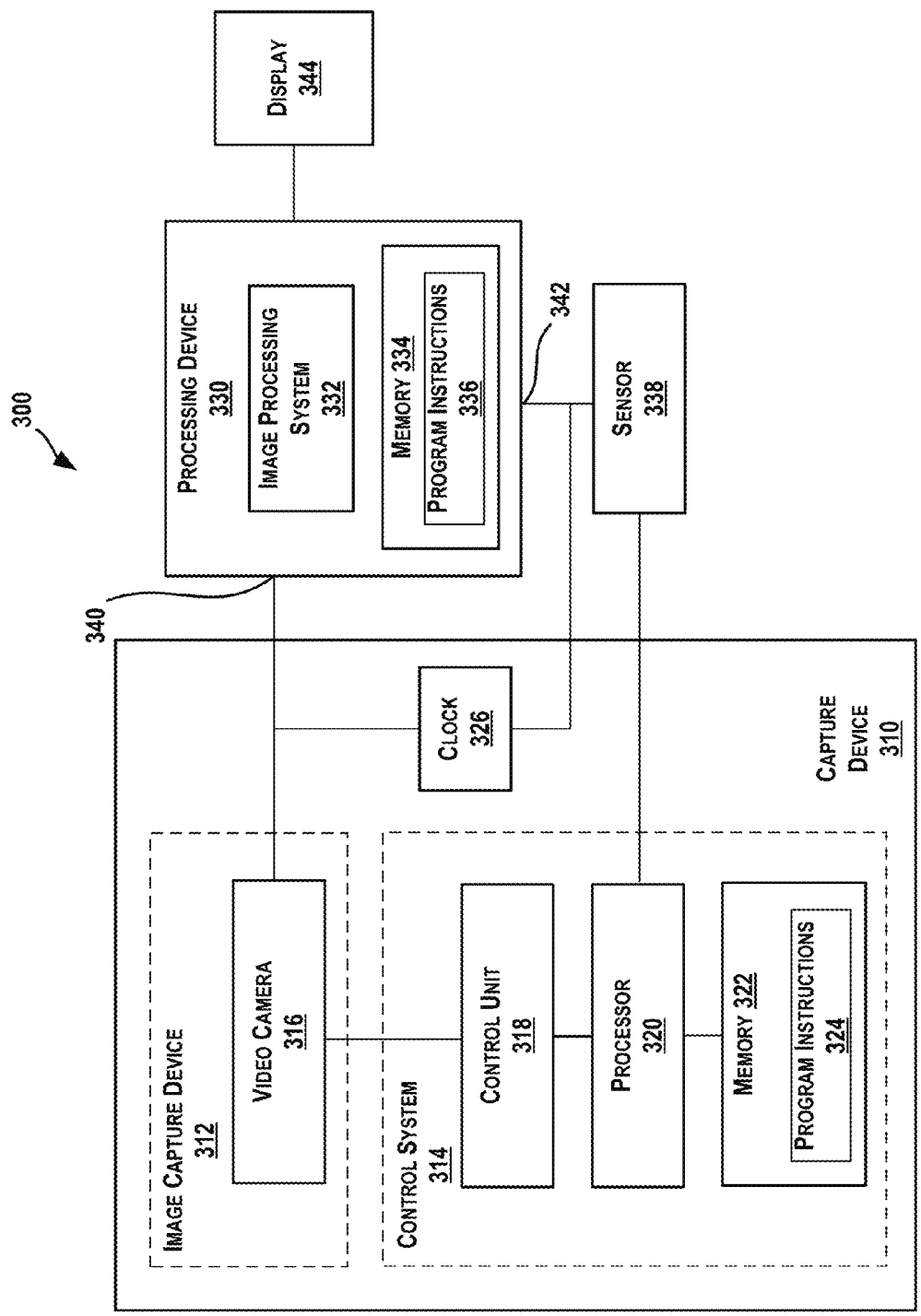
FIG. 3 is a simplified block diagram of a system configured to capture and process video data according to an example embodiment.

FIG. 3 is a simplified block diagram of a system 300 including capture device 310, processing device 330 and at least one sensor 338, according to an example embodiment. The capture device 310 may be any type of device that can capture and process image or video data. For example, the capture device 310 may take the form of or be implemented as part of a head-mountable display, such as the head-mounted devices 102, 152, or 172 that are described with reference to FIGS. 1A to 1G.

The capture device 310 may include an image capture device 312 that includes a video camera 316 configured to capture video data, and a control system 314. Control system 314 may include a control unit 318, a processor 320 and a memory 322. The control unit 318 may be configured, at least in part, to cause the video camera 316 to capture video data and to control at least one image capture setting of the video camera 316. Video data captured by the video camera 316 in the image capture device 312 may be used to generate a video file. The processor 320 may be any type of processor, such as a micro-processor or a digital signal processor, for example. The processor 320 may receive biometric data from one or more sensors 338. At least one clock 326, or other timing device, may also be provided for synchronizing the video camera 316 and sensor 338 outputs. Memory 322 may be provided as a non-transitory computer-readable media such as computer-readable media that stores data for short periods of time like register memory, processor cache, or random access memory (RAM). Memory 322 may also be provided as a non-transitory computer-readable media that stores program code or data for longer periods of time, such as secondary or persistent long term storage, like read only memory (ROM), optical or magnetic disks, or compact-disc read only memory (CD-ROM), for example. Any other volatile or non-volatile data storage system may also be used. Memory 322 may also be considered a computer-readable storage medium, for example, or a tangible storage device.

Sensor 338 may include any type of sensor capable of detecting biometric data from a user of the capture device 310. Biometric data may include any data comprising or related to the sensory, physiological, biological, behavioral, health, motion, context or other measurable characteristics, phenomena or response of a living subject or a function of the living subject. Biometric data may be gathered from direct measurement of an aspect or characteristic of the body, or any data indicative of the movement or context of a body. For example, biometric data may include heart rate, pulse rate, respiration rate, body temperature, perspiration, eye movements, blinking, muscle flinches or tension, strength of hand grip, etc. Biometric contextual data may include any data indicative of the environment, location, ambient conditions, and status of the user, including location such as GPS (or other location-tracking) data, elevation, type of movement (i.e. walking, driving, flying, etc.), type of activity (running, biking, swimming, etc.), weather, ambient temperature, ambient light intensity, time of day, height of a user, weight of a user, age of a user, etc. Biometric motion-related data may include speed or direction of travel, change in altitude, acceleration, cadence, direction or intensity of movement of the body, orientation of the body, gravitational and inertial forces acting on the body, rotation, etc.

In one aspect, the one or more sensors 338 for sensing biometric data may include one or more of a heart rate monitor, a respiration rate sensor, a thermometer, a perspiration sensor (such as a galvanic skin response sensor), a microphone, a decibel meter, a bone conducting transducer, an electromyograph, a strain gauge, an eye-detection sensor, a pulse oximeter, a Doppler device, an eye-tracking device, etc. Sensors 338 for sensing motion-related biometric data may include one or more movement or positioning sensors, such as, an accelerometer, an inertial measurement unit (IMU), a proximity sensor; a microphone; a gyroscope, a magnetometer, an optical sensor, an ultrasonic sensor, an odometer, and a pedometer. Such motion sensors may also detect the position and orientation of a user of the device without necessarily detecting "movement." Further, the one or more sensors 338 for detecting contextual-related biometric data may include one or more of a location-determination sensor, a light intensity sensor, a clock and a sensor configured to receive an input from a user (such as whether she is flying, travelling in a car, walking, etc.).

Sensor 338 may be integral to or separate from the capture device 310, as shown in FIG. 3. For example, the one or more sensors may be integrated on an HMD, or may be remote to the HMD (such as biometric sensors placed on other portions of the body or in communication with the body). The one or more sensors 338 may also be provided on a computing device remote from the HMD (such as a remote device such as a smartphone having location tracking and internet capabilities).

The processing device 330 may include an image processing system 332 and a memory 334 having program instructions 336 stored thereon. The image processing system 332 may be any type of processor, such as a micro-processor or a digital signal processor, for example. Memory 334 may be provided as a non-transitory computer-readable media such as computer-readable media that stores data for short periods of time like register memory, processor cache, or random access memory (RAM). Memory may also be provided as a non-transitory computer-readable media that stores program code or data for longer periods of time, such as secondary or persistent long term storage, like read only memory (ROM), optical or magnetic disks, or compact-disc read only memory (CD-ROM), for example. Any other volatile or non-volatile data storage system may also be used. Memory 334 may also be considered a computer-readable storage medium, for example, or a tangible storage device.

An interface 340 is configured to receive video data generated by the image capture device 340, such as by video camera 316. Biometric data detected by the one or more sensors 338 may be received by interface 342 of the processing device 330. The processing device 330 is configured to process the received video data, with at least one type of image processing, based, at least in part, on the received biometric data, to generate edited video data. The video data and the biometric data are generated synchronously and may be appropriately labelled with time synchronization data by the clock 326, for example, indicating a timing relationship between the biometric data and the video data. Processing of the video data by the processing device 330 may further be based on the time synchronization data.

The processing device 330 may be implemented as part of or on the same platform as the capture device 310, or may be separate from the capture device 310, as shown in FIG. 3. For example the processing device may be implemented as part of or take the form of a head-mountable device (HMD) along with the capture device 310. Alternatively, the processing device 330 may also be provided on a computing device remote from the HMD (such as a remote computing device such as a personal computer, laptop computer, tablet computer, or cellular phone). The processing device 330 may also be implemented as or take the form of a cloud server. In some embodiments, processing device 330 may receive the video, sensor or synchronization data wirelessly according to one or more wireless standards or protocols, such as, but not limited to, RFID, Bluetooth, Wi-Fi, ZigBee, WiMax, or a Wireless Wide Area Network (e.g., TDMA, CDMA, GSM, UMTS, EV-DO, LTE), etc. In other embodiments, processing device 330 may receive the video, sensor and synchronization data by one or more wired protocols such as, but not limited to, a Universal Serial Bus protocol, a Registered Jack protocol (e.g., RJ-25), or a wired Local Area Network protocol (e.g., Ethernet). In other examples, video, sensor and synchronization data may be received by the processing device from a portable storage device such as a memory card, flash drive, or zip drive.

In example embodiments, biometric data collected by the one or more sensors 338 may be used by the system 300 in at least two ways to create a more interesting or sensory-representative video composition. In one aspect, the biometric data may be used to control at least one image-capture setting of the image capture device 312, which may include controlling image capture software or hardware on the image capture device 312. The image capture properties may include, at least, the rate of frame capture and the resolution (e.g., image or spatial). In another aspect, biometric data received from the one or more sensors 338 may be used for assisted post-capture image or audio editing by the processing device 330. Biometric data from the one or more sensors 338 and other inputs may be synchronously recorded with the video and audio data and may essentially "tag" the data with processing cues. These "tags" may be used post-capture to automatically edit or suggest edits to the image and audio data. The image processing applied by the image processing system 332 may include, but is not limited to, fast motion effects, slow motion effects, blur effects, color calibration, light intensity calibration, fade-in or fade-out effects, frame cutting, frame rate conversion, white point conversion, color space conversion, noise reduction, detail enhancement, edge enhancement, and motion compensation.

The manner in which the image capture properties of the image capture device 312 are controlled and the manner in which the image processing is applied by the image processing system 332, based on the biometric data, may depend on qualitative and quantitative properties of the received biometric data. The control system 314 of the capture device 310 and the image processing system 332 of the processing device 330 may be configured to control image capture properties and apply image processing, respectively, based on certain logic programmed on the devices. The logic may dictate that, upon receipt of a certain type of biometric data and at a certain level, the image processing system should apply a certain type of image processing and in a certain manner. This logic may be based on certain knowledge, observations, conventions, standards or preferences that may allow the ultimate video data to better reflect the emotions, perceptions and senses of the user or create a more interesting composition. For example, certain observations may be made that biometric data reflecting elevated heart, respiration or pulse rate, increased perspiration, and increased cadence of movement indicates that the wearer or user of the device is engaged in a high level of activity or is experiencing excitement. Certain conventions may suggest that these experiences and perceptions may be translated into the captured video and audio data by, for example, replaying the video or audio data in slow motion.

To achieve one or more of these functions, the control system 314 of the capture device 310 may be configured to receive biometric data from the one or more sensors 338 and, while the image-capture device 312 is capturing video data, control at least one image-capture setting of the image capture device 312 based, at least in part, on the biometric data. The at least one image-capture setting, which may include the rate of frame capture and the resolution of, for example, the video camera 316, affects the captured video data. The control system 314 may further be configured to cause the sensors 338 to generate the biometric data while the image-capture device 312 captures the video data.

Specifically, in operation, the processor 320 may execute one or more program instructions 324 stored in memory 322, which may include certain program logic. Execution of these program instructions 324 by the processor 320 may cause the image capture device 312 to capture video data, such as with video camera 316. The instructions may further cause the capture device 310 to receive biometric data from the one or more sensors 338. The biometric data may be generated synchronously with the video data generated by the video camera 316. Clock 326 may provide time-synchronization data that indicates a timing relationship between the biometric data and the video data. The processor 320 may receive the biometric data from the one or more sensors 338 and execute the program instructions 324, which may relate to when and how the received biometric data is to be used by the control system 314. While the image-capture device 316 continues to capture video data, execution of the program instructions 324 by the processor may cause the control unit 318 of the control system 314 to control at least one image-capture setting of the image capture device 312.

In an example embodiment, the control unit 318 is configured to control at least one image capture setting based, at least in part, on the biometric data from the sensor 338. Data taken from the sensor 338, such as heart rate, may be used to control software or hardware of the capture device 310. For example, the control unit 318 may be configured to increase the rate of image frame capture of the video camera 316 upon receiving biometric data indicative of a higher than normal heart rate. An increased heart rate may indicate that the user is operating at a high level of activity, is frightened or excited, or is in some other situation in which a high frame rate or higher resolution may be desirable. In response, the control unit 318 may increase the resolution or frame rate of the video camera 316. In another example, upon receiving biometric data indicative of falling, such as from an IMU located on or in communication with capture device 310, the control unit 318 may increase the rate of image frame capture of the video camera 316. This portion of increased frame rate video may later be used to create a "slow motion" section of the resulting video file, thereby highlighting the user's free-fall. In a further example, the control system may be configured to increase the rate of image frame capture based, at least in part, on receiving biometric data indicative of a higher than normal respiration rate, which may also indicate increased activity or excitement. Certain thresholds relating to the biometric data, such as normal heart and respiration rates, may be stored in memory 322. Many other inferences may be made between the collected biometric data and the activity level, emotions or sensory perceptions of users of the capture device 310.

To further achieve one or more of the functions described above, the image processing system 332 may be used, post-capture, to enhance the video data by applying one or more image processing techniques. In operation, the image processing system 332 may execute one or more program instructions 336 stored in memory 334 on the processing device 330. Execution of these program instructions 336 by the image processing system 332 may cause the processing device 330 to receive video data generated by an image capture device 312, via interface 340. Further, the image processing system may cause the processing device 330 to receive, from the one or more sensors 338, biometric data of a user of the image capture device 312, via interface 342.

The image processing system 332 may further be configured to apply image processing to the video data based, at least in part, on the biometric data, and to generate edited video data therefrom. Visual emphasis (or de-emphasis) may be achieved by adjusting the speed of the video, color calibration, light intensity calibration, white point conversion, color space conversion or by applying blur effects, fade-in or fade-out effects, frame cutting, frame rate conversion, noise reduction, detail enhancement, edge enhancement, and motion compensation.

For example, biometric data collected from a heart-rate monitor (HRM) indicating a normal or slower than normal heart rate may cause the image processing system 332 to increase the speed of the video data to generate edited video data. A normal or lower than normal heart rate may indicate that the user may not be engaged in rigorous movement and may not be experiencing anything particularly exciting. In such cases, where the captured video may be considered of less interest, it may be desirable to increase the speed of the video data, for example, as fast playback. Alternatively, biometric data indicating a higher than normal heart rate or sharp increase in the wearer's heart rate may cause the image processing system 332 to slow-down that segment of recorded video to create visual emphasis. In another example, the image processing system may be configured to decrease the speed of the video data to generate edited video data based, at least in part, on receiving biometric data indicative of falling or on receiving biometric data indicative of a higher than normal respiration rate. Visual emphasis may also be achieved by changing the color saturation of the video data. For example, the image processing system 332 may be configured to adjust the color saturation towards yellow based on receiving biometric data indicative of speed of travel.

Further, the image processing applied to the video data may include one or more audio effects, such as audio overlay, noise removal, noise amplification, noise suppression, audio volume adjustment, pitch shift, or time stretching effects. For example, the image processing system may be configured to apply an audio overlay such as music or a heartbeat sound to the video data. The video data may include audio data. In other examples, the image processing system may be configured to suppress or amplify background audio noise present in the video data, such as wind noise or motorcycle noise.

The image processing system 332 may be configured to automatically apply the one or more image processing techniques to the captured video data. In other aspects, the image processing system 332 may be configured to suggest that an image processing be applied based on the biometric data or otherwise "tag" portions of the video data based on the collected biometric data for subsequent manual editing.

Biometric data may be continuously received by the processor 320 and the image processing system 332 and analyzed to determine whether one or more settings of the image capture device should be controlled or if one or more image processing techniques should be applied by the processing device. Similarly, the biometric data can be used to determine if an image capture setting should be returned to normal or if one or more image processing techniques should be ceased.

Further, one of skill in the art will recognize that biometric data of different types received from different types of sensors 338 may be used in conjunction by the capture device 310 and the processing device 330 to achieve their respective functions. For example, biometric data received from a heart-rate monitor indicating an increased heart rate may be checked against biometric data received from one or more motion sensors, such as an optical sensor on a user's bike, to determine if the user is still moving (i.e., still pedaling the bike) to decide if an image processing should be applied. In addition, motion-related biometric data may be used in conjunction with context-related biometric data gathered by one or more sensors. For example, if the system receives biometric data, such as by direct input from the user, indicating that the user is travelling by car, the system may determine that a high speed of travel by the user does not necessarily indicate that an image capture setting should be controlled or image processing should be applied to the video data. Similarly, biometric data indicating increased perspiration may be compared to context-related biometric data indicating a high ambient temperature.

In operation, a user of the image capture device 310 enters video recording mode by, for example, manual input or by speaking a verbal command. As part of the video recording mode, a user interface or one or more graphics may be provided on a display. Where the image capture device 310 takes the form of or includes an HMD, the display may be, for example, an optical see-through display, an optical see-around display, or a video see-through display. The user interface or graphics may indicate that one or more types of biometric data are being received by the image capture device 310. For example, the user interface or graphic may include a heart icon to indicate that heart rate data is being received from a heart-rate sensor. In addition, the user interface or graphics may provide a real-time indication of the biometric data being received. For example, the user interface or graphic may also include a number indicating the wearer's heart rate as sensed by the corresponding sensor. The displayed graphics or interface may be time-synced with the received biometric sensor data such that the numerical value is updated in real time as new sensor data is received.

Additionally or alternatively, an overlaid user interface or graphic 410 may be added to the captured video data by the image processing system 332 as part of the image processing to generate edited video data. The user interface or graphic may include images or icons indicating the type of biometric data that was sensed concurrently with the captured video.

For example, a heart icon may indicate that heart rate data was sensed, a mountain icon may indicate that altitude data was sensed, or a water droplet icon may indicate that perspiration data was sensed. In addition, the user interface or graphic may include an indication or quantification, such as a numerical value, of the sensed biometric data, such as an indication of the wearer's heart rate, respiration rate, speed or cadence of movement, elevation, etc. The edited video data may be output from the image processing system 332 to a display 344 for displaying the edited video data.

Figure 4:
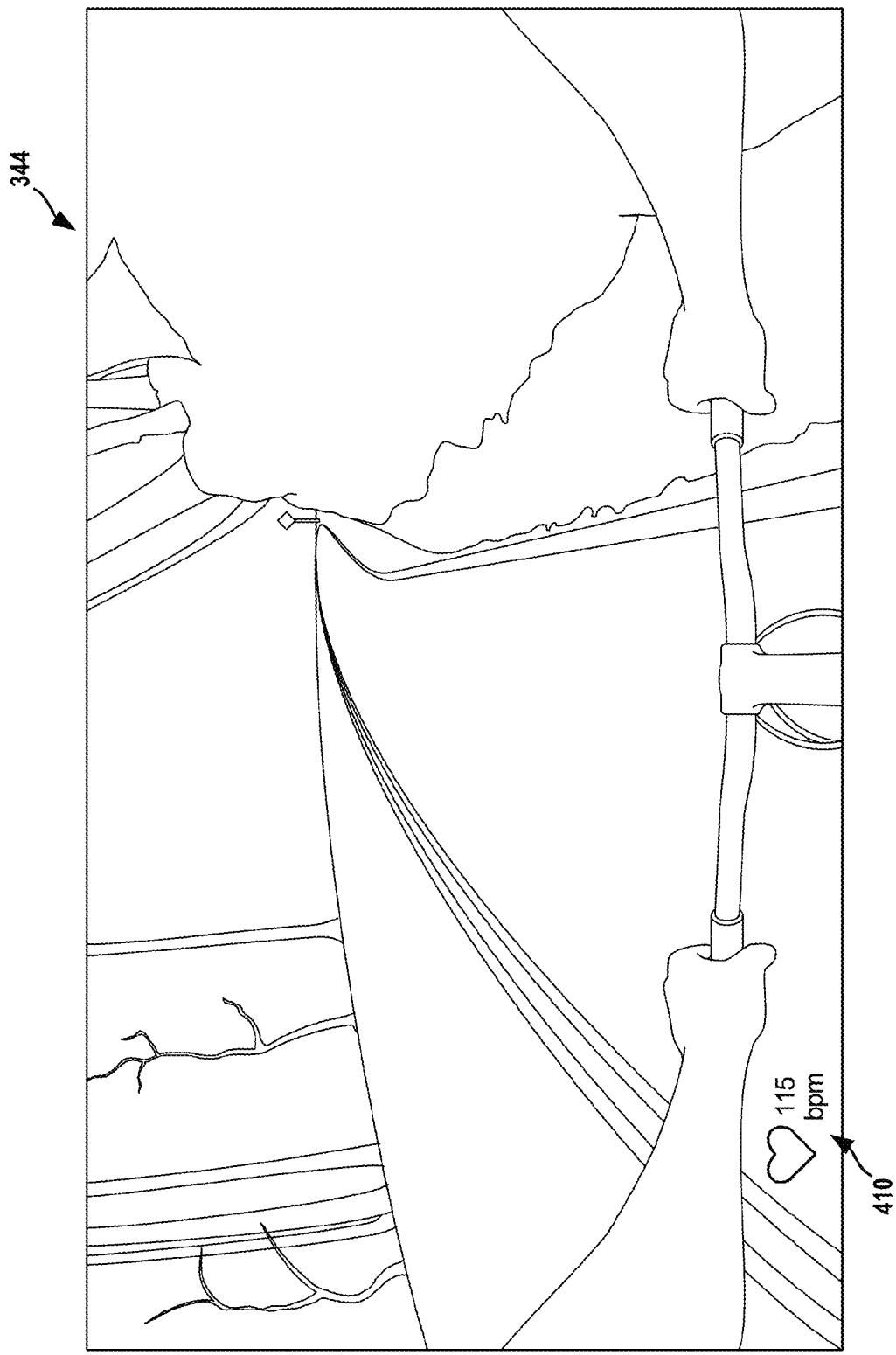
FIG. 4 is a screenshot of an example user interface showing edited video data in accordance to an example embodiment.

As shown in FIG. 4, which illustrates a screenshot of a video display 344, when played back on the display 344, the edited video data will include the user interface or graphic 410. Further, as the sensed biometric data is time synced with the captured video data, the biometric data will also be time synced with the edited video data such that the indication of biometric data overlaid as part of the user interface or graphic will update as the edited video data is replayed. The user interface or graphic may be applied as part of the image processing to the edited video data independently of the user interface or graphic being displayed on the HMD display.

As part of the image processing, music or sounds may be applied to the video data to generate edited video data. For example, a heartbeat sound may be applied to the video data. The user interface or graphic and sound may be applied to the video data prior to other types of the image processing, such as fast or slow motion effects. Accordingly, the applied sound also be sped up or slowed down as part of the image processing along with the captured video data. While illustrated as a separate element, the display 344 may be provided on the same platform as image processing system 332.

IV. Example Methods

Figure 5:
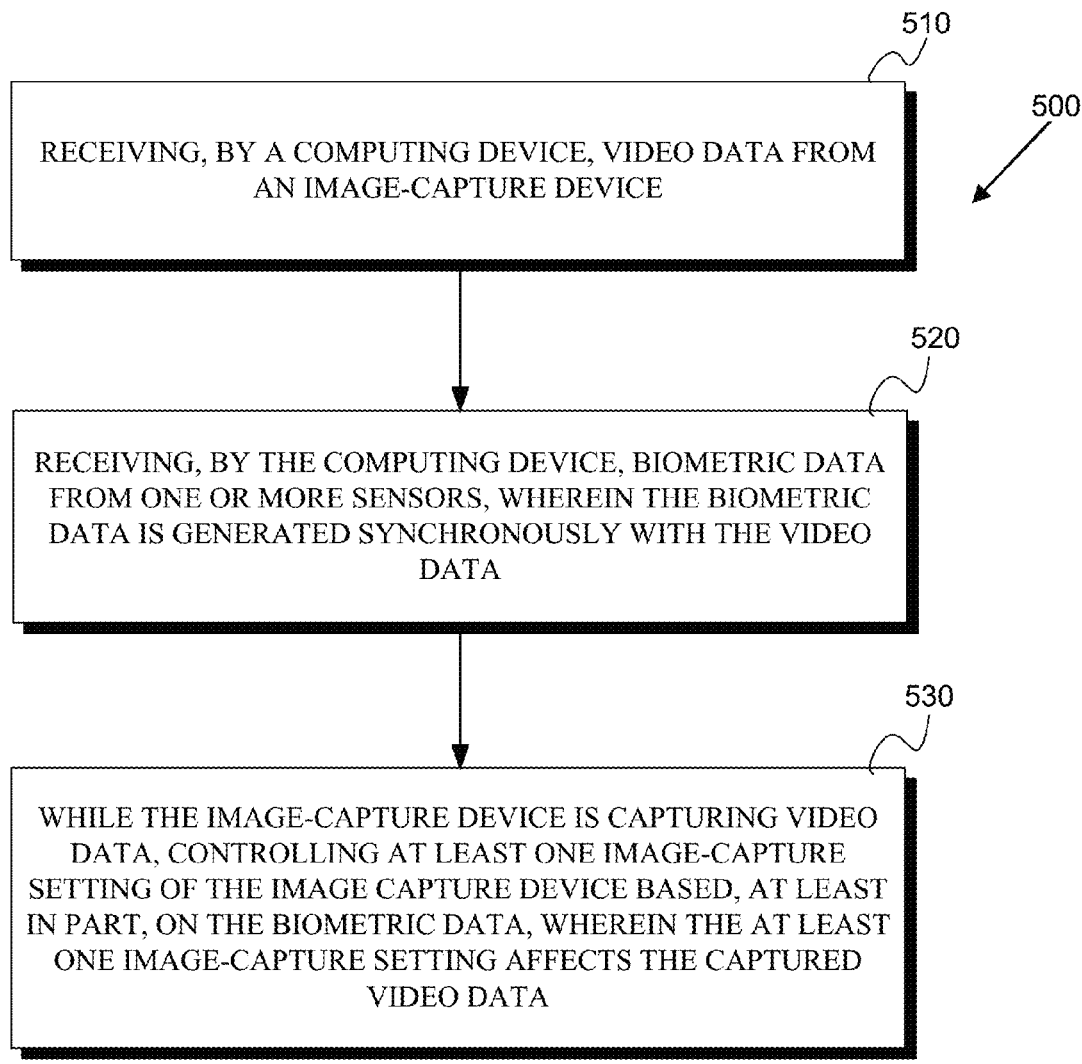
FIG. 5 is a flow chart of an example method, in accordance with an example embodiment.

FIG. 5 is a flow chart illustrating a method 500, according to an example embodiment. Illustrative methods, such as method 500, may be carried out in whole or in part by an HMD, such as the head-mountable devices shown in FIGS. 1A to 1G. Method 500 may be carried out by components of an HMD, such as a capture device 310. Such a capture device may include, for example, an image capture device and a control system having a control unit, a processor and program instructions stored on a non-transitory computer-readable medium. However, an HMD's capture device may additionally or alternatively include other components. Further, an example method or portions thereof may be carried out by additional components of an HMD. Yet further, an example method, or portions thereof, may be carried out by a capture device that is in communication with an HMD. An example method may also be carried out by other types of computing devices or combinations of computing devices including other types of wearable computing devices as well.

In a first step, video data is received by a computing device from an image-capture device, such as image capture device 312. (510). In addition, biometric data, which is generated synchronously with the video data, is received by the computing device from one or more sensors. (520). As described above, the one or more sensors (such as sensors 338) may be any sensor configured to detect biometric data, which may include any data related to the sensory, physiological, behavioral, health, movement, context or other measurable characteristics of a user of the image capture device or a function of the user. While the image-capture device is capturing video data, at least one image-capture setting of the image capture device may be controlled based, at least in part, on the biometric data, thereby affecting the captured video data. (530). The at least one image capture setting includes rate of image frame capture, and resolution.

Figure 6:
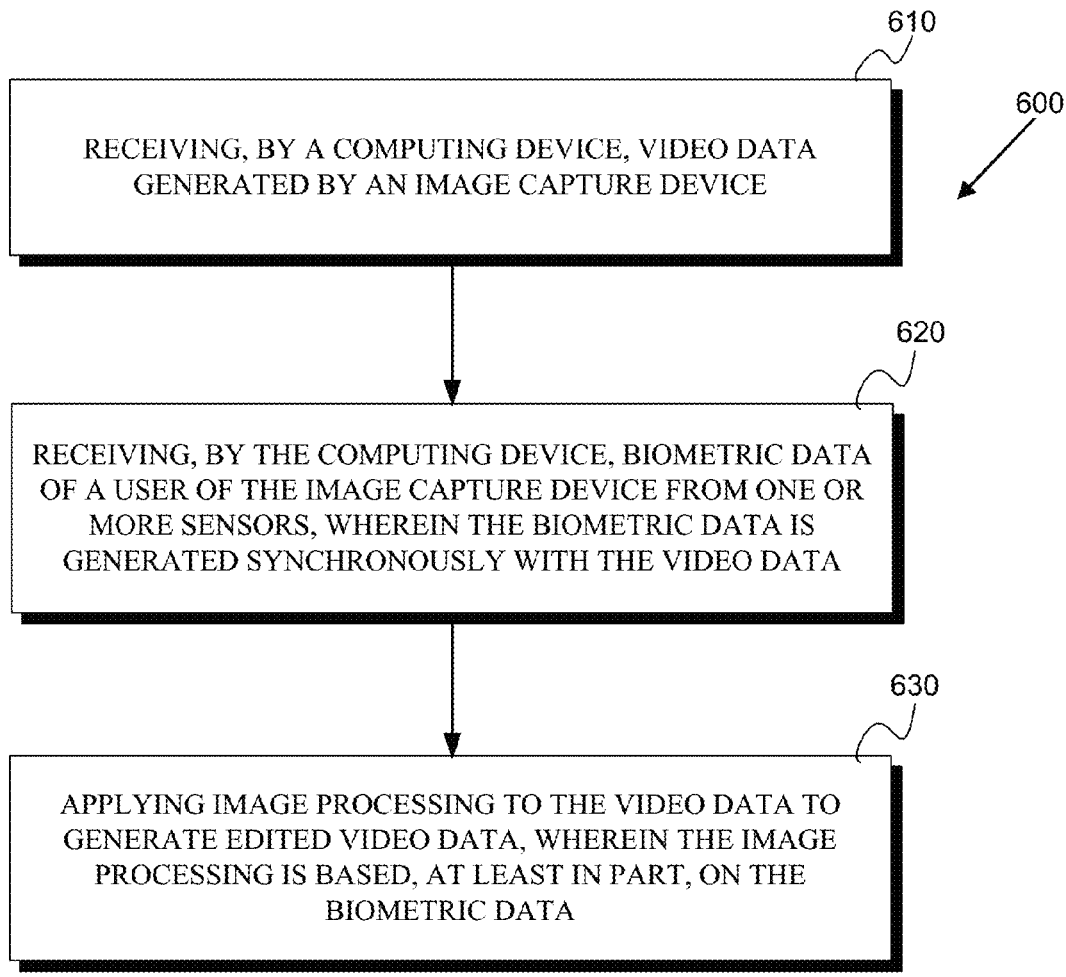
FIG. 6 is a flow chart of an example method, in accordance with an example embodiment.

FIG. 6 is a flow chart illustrating a method 600, according to an example embodiment. Illustrative methods, such as method 600, may be carried out in whole or in part by a computing device. The computing device may be an HMD, such as the head-mountable devices shown in FIGS. 1A to 1G. Method 600 may be carried out by components of an HMD, such as a processing device 330. Such a processing device may include, for example, an image processing system and program instructions stored on a non-transitory computer-readable medium. However, an HMD's processing device may additionally or alternatively include other components. Further, an example method or portions thereof may be carried out by additional components of an HMD. Yet further, an example method, or portions thereof, may be carried out by a processing device that is remote from an HMD, such as in system 300. An example method may also be carried out by other types of computing devices or combinations of computing devices including other types of wearable computing devices as well.

In a first step, video data generated by an image capture device is received by a computing device. (610). Biometric data of a user of the image capture device is received by the computing device from one or more sensors. (620). The biometric data is generated synchronously with the video data. Image processing is applied to the video data based, at least in part, on the biometric data to generate edited video data (630). As described above, the image processing may include, but is not limited to: fast motion effects, slow motion effects, blur effects, color calibration, light intensity calibration, fade-in or fade-out effects, frame cutting, frame rate conversion, white point conversion, color space conversion, noise reduction, detail enhancement, edge enhancement, and motion compensation. The edited video data may be output to a user interface, such as a video screen, as shown in FIG. 4.

Time-synchronization that indicates a timing relationship between the biometric data and the video data may also be received. This synchronization data may allow the image processing system to align the user's biometric signals with the video that was captured at that time and apply biometrically-relevant image processing to the video data. Accordingly, the image processing system may further base the image processing of the video data on the time-synchronization data.

Wearable devices implementing the methods and or devices described above have many possible applications where adjusting image capture settings or applying relevant image processing to the video data may be desirable. One such application may be in the field of extreme sports where users may desire to take point-of-view action video of their own perspective. Take, for example, a person using an HMD having a capture device, such as capture device 310, to capture point-of-view video while mountain biking. Sensors in communication with the capture device, will detect biometric signals from the user, such as heart rate, pedaling speed, level of perspiration, and level of auditory noise. Upon receipt of biometric data indicating that the user has an increased heart rate and increased auditory response, the capture device may increase the rate of frame capture of the video camera, from, for example, 30 frames per second to 120 frames per second. This action by the capture device may be based on logic that an increased heart rate and an increased auditory response (e.g., yelling or shouting) indicate high emotion or excitement by the user, which may further indicate exciting, valuable or interesting video data. By increasing the frame rate, this portion of video data may subsequently be used to create a slow-motion segment of the video file, which may add visual interest and emotional context to the video. The video file generated from this recorded session will include some portion at 30 frames per second and some portions at 120 frames per second.

Further, image processing may further be applied to the video data by a processing device, such as device 330. In the example described above, an image processing system may, in response to the biometric data of the user indicating increased heart rate and increased auditory response, apply slow motion image processing or color enhancement image processing, as examples. The processing device may also suggest to a user that certain image processing be applied to the video data. Alternatively, based on biometric data received from one or more optical motion sensors positioned on the user's bike indicating that the user has ceased pedaling for an extended period of time, the processing device may discard (or cut) certain frames. This action by the processing device may be based on logic that a cessation in movement indicates relatively unexciting or uninteresting video data. Many other applications are contemplated.

V. Conclusion

In the figures, similar symbols typically identify similar components, unless context indicates otherwise. The illustrative embodiments described in the detailed description, figures, and claims are not meant to be limiting. Other embodiments can be utilized, and other changes can be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

With respect to any or all of the message flow diagrams, scenarios, and flow charts in the figures and as discussed herein, each step, block or communication may represent a processing of information or a transmission of information in accordance with example embodiments. Alternative embodiments are included within the scope of these example embodiments. In these alternative embodiments, for example, functions described as steps, blocks, transmissions, communications, requests, responses, or messages may be executed out of order from that shown or discussed, including in substantially concurrent or in reverse order, depending on the functionality involved. Further, more or fewer steps, blocks or functions may be used with any of the message flow diagrams, scenarios, and flow charts discussed herein, and these message flow diagrams, scenarios, and flow charts may be combined with one another, in part or in whole.

A step or block that represents a processing of information may correspond to circuitry that can be configured to perform the specific logical functions of a herein-described method or technique. Alternatively or additionally, a step or block that represents a processing of information may correspond to a module, a segment, or a portion of program code (including related data). The program code may include one or more instructions executable by a processor for implementing specific logical functions or actions in the method or technique. The program code or related data may be stored on any type of computer-readable medium, such as a storage device, including a disk drive, a hard drive, or other storage media.

The computer-readable medium may also include non-transitory computer-readable media such as computer-readable media that stores data for short periods of time like register memory, processor cache, or random access memory (RAM). The computer-readable media may also include non-transitory computer-readable media that stores program code or data for longer periods of time, such as secondary or persistent long term storage, like read only memory (ROM), optical or magnetic disks, or compact-disc read only memory (CD-ROM), for example. The computer-readable media may also be any other volatile or non-volatile storage systems. A computer-readable medium may be considered a computer-readable storage medium, for example, or a tangible storage device.

Moreover, a step or block that represents one or more information transmissions may correspond to information transmissions between software or hardware modules in the same physical device. However, other information transmissions may be between software modules or hardware modules in different physical devices.

In situations in which the systems discussed here collect personal information about users, or may make use of personal information, the users may be provided with an opportunity to control whether programs or features collect user information (e.g., information about a user's social network, social actions or activities, profession, a user's preferences, or a user's current location), or to control whether and/or how to receive content from the content server that may be more relevant to the user. In addition, certain data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined. Thus, the user may have control over how information is collected about the user and used by a content server.

We claim:

1. A computing device, comprising:
an interface configured to receive video data that is generated by an image capture device;
an interface configured to receive, from one or more sensors, biometric data of a user of the device generated during capture of the received video data, wherein the biometric data is generated synchronously with the video data, wherein a first portion of the biometric data indicates a faster than normal heartrate, and a second portion of the biometric data indicates a normal or slower than normal heartrate, and wherein the first portion of the biometric data corresponds to a first portion of the video data and the second portion of the biometric data corresponds to a second portion of the video data;
an image processing system configured to apply image processing to the video data to generate edited video data, wherein the image processing system is configured to generate edited video data comprising the first portion of the video data at a first frame rate and the second portion of the video data at a second frame rate, wherein the second frame rate is less than the first frame rate; and generate a video file comprising the edited video data for subsequent playback at a playback frame rate equal to the second frame rate, such that the first portion of the video data is played back in slow motion.

2. The computing device of claim 1, further comprising: an interface configured to receive time-synchronization data that indicates a timing relationship between the biometric data and the video data, wherein the image processing of the video data is further based on the time-synchronization data.

3. The computing device of claim 1, wherein the computing device is implemented as part of or takes the form of a head-mountable device (HMD).

4. The computing device of claim 1, wherein the computing device is implemented as or takes the form of a cloud server.

5. The computing device of claim 1, wherein the image processing system is further configured to:
apply image processing based, at least in part, on biometric data comprising one or more of: (a) heart rate, (b) respiration rate, (c) body temperature, (d) level of perspiration, (e) muscle movement, (f) eye movement, (g) blinking, and (h) speech.

6. The computing device of claim 5, wherein the one or more sensors comprise one or more biometric sensors selected from the group consisting of: (a) a heart rate monitor, (b) a respiration rate sensor, (c) a thermometer, (e) a perspiration sensor, (f) a microphone, (g) a decibel meter, (h) a bone conducting transducer, (i) an electromyograph, (j) a strain gauge, and (k) an eye-detection sensor.

7. The computing device of claim 1, wherein the one or more sensors comprise one or more movement or positioning sensors selected from the group consisting of: (a) an accelerometer, (b) an inertial measurement unit, (c) a proximity sensor; (d) a microphone; (e) a gyroscope, (f) a magnetometer, (g) an optical sensor, (h) an ultrasonic sensor, (i) an odometer, and (j) a pedometer.

8. The computing device of claim 7, wherein the one or more sensors comprise one or more contextual sensors selected from the group consisting of: (a) a location-tracking sensor, (b) light intensity sensor, (c) a clock, and (d) a sensor configured to receive an input from a user.

9. The computing device of claim 1, wherein the image processing system is further configured to:
apply image processing based, at least in part, on biometric data comprising one or more of: (a) location, (b) ambient light intensity, (c) time of day, (d) a user's mode of travel, (e) a type of activity a user is participating in, (f) height of a user, (g) weight of a user, and (h) age of a user.

10. The computing device of claim 1, wherein the image processing comprises at least one of: (a) fast motion effects, (b) slow motion effects, (c) blur effects, (d) color calibration, (e) light intensity calibration, (f) fade-in or fade-out effects, (g) frame cutting, (h) frame rate conversion, (i) white point conversion, (j) color space conversion, (k) noise reduction, (l) detail enhancement, (m) edge enhancement, or (n) motion compensation.

11. The computing device of claim 10, wherein the image processing system is configured to increase a speed of the video data to generate edited video data based, at least in part, on receiving biometric data indicative of a normal or slower than normal heart rate.

12. The computing device of claim 10, wherein the image processing system is configured to decrease a speed of the video data to generate edited video data based, at least in part, on receiving biometric data indicative of a higher than normal heart rate.

13. The computing device of claim 10, wherein the image processing system is configured to decrease a speed of the video data to generate edited video data based, at least in part, on receiving biometric data indicative of falling.

14. The computing device of claim 10, wherein the image processing system is configured to decrease a speed of the video data to generate edited video data based, at least in part, on receiving biometric data indicative of a higher than normal respiration rate.

15. The computing device of claim 10, wherein the image processing system is configured to adjust a color saturation of the video data to generate edited video data based, at least in part, on receiving biometric data indicative of speed of travel.

16. The computing device of claim 1, wherein the image processing comprises one or more audio effects including: (a) audio overlay, (b) noise removal, (c) noise amplification, (d) noise suppression, (e) audio volume adjustment, (f) pitch shift, and (g) time stretching.

17. The computing device of claim 1, further comprising a display configured to display at least one of: an indication of the biometric data and the edited video data.

18. The computing device of claim 1, wherein the generated video file specifies that the playback frame rate is the second frame rate, such that a portion of the generated video file corresponding to the first portion appears in slow motion when played back at the second frame rate.

19. A method comprising:
receiving, by a computing device, video data generated by an image capture device;
receiving, by the computing device, from one or more sensors, biometric data of a user of the image capture device that is generated during capture of the received video data, wherein the biometric data is generated synchronously with the video data, wherein a first portion of the biometric data indicates a faster than normal heartrate, and a second portion of the biometric data indicates a normal or slower than normal heartrate, and wherein the first portion of the biometric data corresponds to a first portion of the video data and the second portion of the biometric data corresponds to a second portion of the video data; and
applying image processing to the video data to generate edited video data, wherein the image processing system is configured to generate edited video data comprising the first portion of the video data at a first frame rate and the second portion of the video data at a second frame rate, wherein the second frame rate is less than the first frame rate; and
generating a video file comprising the edited video data for subsequent playback at a playback frame rate equal to the second frame rate, such that the first portion of the video data is played back in slow motion.

20. The method of claim 19, further comprising:
receiving time-synchronization data that indicates a timing relationship between the biometric data and the video data, wherein the image processing of the video data is further based on the time-synchronization data.

21. The method of claim 19, further comprising:
displaying, on a display in communication with the computing device, one or more of: an indication of the biometric data and the edited video data.

22. A non-transitory computer readable medium having stored therein instructions executable by a processor to cause a computing device to perform functions comprising:

receiving video data generated by an image capture device;

receiving, from one or more sensors, biometric data of a user of the image capture device that is generated during capture of the received video data, wherein the biometric data is generated synchronously with the video data, wherein a first portion of the biometric data indicates a faster than normal heartrate, and a second portion of the biometric data indicates a normal or slower than normal heartrate, and wherein the first portion of the biometric data corresponds to a first portion of the video data and the second portion of the biometric data corresponds to a second portion of the video data; and applying image processing to the video data to generate edited video data wherein the image processing system is configured to generate edited video data comprising the first portion of the video data at a first frame rate and the second portion of the video data at a second frame rate, wherein the second frame rate is less than the first frame rate; and generating a video file comprising the edited video data for subsequent playback at a playback frame rate equal to the second frame rate, such that the first portion of the video data is played back in slow motion.

23. The non-transitory computer readable medium of claim 22, wherein the functions further comprise:

receiving time-synchronization data that indicates a timing relationship between the biometric data and the video data, wherein the image processing of the video data is further based on the time-synchronization data.

* * * * *